(12) United States Patent
Pichler et al.

(10) Patent No.: US 8,290,568 B2
(45) Date of Patent: Oct. 16, 2012

(54) METHOD FOR DETERMINING A PROPERTY MAP OF AN OBJECT, PARTICULARLY OF A LIVING BEING, BASED ON AT LEAST A FIRST IMAGE, PARTICULARLY A MAGNETIC RESONANCE IMAGE

(75) Inventors: Bernd Pichler, Scheyern (DE); Matthias Hofmann, Tübingen (DE); Bernhard Schölkopf, Tübingen (DE); Florian Steinke, Herrenberg (DE)

(73) Assignee: Eberhard-Karls-Universitat Tubingen Universitatsklinikum, Tubingen (DE)

( * ) Notice: Subject to any disclaimer, the term of this patent is extended or adjusted under 35 U.S.C. 154(b) by 534 days.

(21) Appl. No.: 12/351,429

(22) Filed: Jan. 9, 2009

(65) Prior Publication Data

US 2010/0049032 A1 Feb. 25, 2010

Related U.S. Application Data

(63) Continuation of application No. PCT/EP2007/005455, filed on Jun. 21, 2007.

(30) Foreign Application Priority Data

Jul. 12, 2006 (DE) .......................... 10 2006 033 383

(51) Int. Cl.
*A61B 5/05* (2006.01)
(52) U.S. Cl. ........................................ 600/411; 600/410
(58) Field of Classification Search ........................ None
See application file for complete search history.

(56) References Cited

U.S. PATENT DOCUMENTS 6,740,883 B1 5/2004 Stodilka et al.
(Continued)

FOREIGN PATENT DOCUMENTS
EP 1105750 6/2001

OTHER PUBLICATIONS

Zhang, X. et al.: "Application of support vector machines in classification of magnetic resonance images". International Journal of Computers and Applications, vol. 28, No. 2, 2006, pp. 122-128.

(Continued)

*Primary Examiner* — Long V. Le
*Assistant Examiner* — Bradley Impink
(74) *Attorney, Agent, or Firm* — McNeely, Hare & War LLP; Kevin J. McNeely (57) ABSTRACT

It is disclosed a system and method (12) for determining a property map (82) of an object, particularly a human being, based on at least a first image (84), particularly an magnetic resonance (MR) image, of the object. In the method (12), a structure of reference pairs is defined in a first step (96), wherein each reference pair (16-26) comprises at least two entries (62). The first entry represents a property value, particularly an attenuation value. The second entry (62) preferably represents a group of image points (67) belonging together, which is extracted particularly from MR images (28) and comprises an interesting image point corresponding to the property value. In another step (98) of the method (12) a plurality of training pairs (16-26) is provided. A structure of the training pairs (16-26) corresponds to the structure of reference pairs, and the entries of respective training pairs (16-26) are known. In another step (100) of the method (12), an assignment between the first entries and the other entries (62-66) of the training pairs (16-26) is determined by machine learning, thus allowing prediction of a property value (88) corresponding to an arbitrary point (90) of the first image (84).

19 Claims, 6 Drawing Sheets

U.S. PATENT DOCUMENTS

| | | |
|---|---|---|
| 6,950,544 B2 | 9/2005 | Ashton |
| 2002/0165837 A1 | 11/2002 | Zhang et al. |
| 2003/0212320 A1* | 11/2003 | Wilk et al. .................... 600/407 |
| 2004/0086199 A1* | 5/2004 | Stearns ......................... 382/289 |
| 2005/0113667 A1* | 5/2005 | Schlyer et al. ................ 600/411 |
| 2006/0058641 A1 | 3/2006 | Krieg et al. |
| 2006/0237652 A1* | 10/2006 | Kimchy et al. .......... 250/363.02 |
| 2008/0135769 A1* | 6/2008 | Rosen ...................... 250/363.09 |

OTHER PUBLICATIONS

Chan, Ian et al.: "Detection of prostate cancer by integration of line-scan diffusion, T2-mapping and T2-weighted magnetic resonance imaging; a multichannel statistical classifier". Medical Physics, vol. 30, No. 9, Sep. 2003, pp. 2390-2398.

Ou, Tan et al.: "Automatic segmentation and classification of human brain images based on TT atlas". Proceedings of the 20th Annual International Conference of the IEEE Engineering in Medicine and Biology Society, vol. 20, No. 2, 1998, pp. 700-702.

Zaidi, Habib et al.: "Magnetic resonance imaging-guided attenuation and scatter corrections in three-dimensional brain positron emission tomography". Medical Physics, vol. 30, No. 5, May 2003, pp. 937-948.

* cited by examiner

METHOD FOR DETERMINING A PROPERTY MAP OF AN OBJECT, PARTICULARLY OF A LIVING BEING, BASED ON AT LEAST A FIRST IMAGE, PARTICULARLY A MAGNETIC RESONANCE IMAGE

RELATED APPLICATIONS

This is a continuation application of the co-pending international application PCT/EP2007/005455 filed on Jun. 21, 2007 which claims priority of the German patent application DE 10 2006 033 383 filed on Jul. 12, 2006 which is fully incorporated herewith by reference.

BACKGROUND OF THE INVENTION

The invention relates to a method for determining a property map of an object, particularly of a living being, based on at least a first image, particularly a magnetic resonance (MR) image.

RELATED PRIOR ART

The method in accordance with the present invention is to be used, among other things, for evaluating Positron Mission Tomography (PET) images which are recorded by means of a PET/MR scanner currently being developed. This PET/MR scanner allows to shoot PET and MR images, both images being shot simultaneously or temporarily separated, and depicting a roughly identical image patch. The (non-corrected) PET image is to be corrected by the aid of an attenuation map, thus allowing subsequent usage of the corrected, quantitatively precise, PET image, for example, with medical diagnose. Calculation of an attenuation map based on MR images is one possible application of the method of the present invention.

PET is an image-providing method which is used in nuclear medicine for generating a sectional image of living organism such as human beings or animals. The shot PET image represents a "functional" mapping of a body section of the living organism since the image provides insights into biochemical and physiological processes such as metabolism processes of an organ.

In order to generate a PET image, an organism to be examined is given a radioactive pharmaceutical product such as $^{15}O$ or $^{18}F$ having half-value period in the range of, for example, 20 minutes. Positrons are emitted ($\beta^+$ decay) when radioactive pharmaceutical products decay, the positrons annihilating with electrons after a short distance within the body and producing two gamma quanta, γ-quanta. These two γ-quanta depart from each other under an angle of 180°, and impinge at oppositely arranged positions of an annular detector. The sectional image of the body section to be examined is formed by a plurality of such coincidence registrations within the detector.

For achieving a quantitatively accurate PET image two effects have to be taken into account which are caused by the recording technique. The γ-quanta, caused by the electron/positron annihilation, experience an attenuation within the body due to absorption. Also, the detection of γ-quanta is influenced by multiple-scattering processes of the γ-quanta, such as Compton scattering, within the body. The share of the scattered γ-quanta depends on the γ-energy of the used radioactive isotope, the density of the layer to be traversed, and the attenuation value thereof.

Correction of attenuation and scattering of the shot PET image corrects both effects at least partially. A known correction for the entire PET image is performed by the add of a so-called attenuation map which provides correction values for the PET image in a point manner for computationally considering attenuation and scattering effects of γ-quanta within the body.

MR is another image-providing method for generating a sectional image of a body section to be examined. With this method (transversal and longitudinal) relaxation times $T_1$ and $T_2$ of nuclear spins are measured which are excited by high frequency pulses. The MR image contains information on anatomical structures of the body section to be examined, since MR offers a particularly high contrast between tissue, bones and soft parts. This contrast is determined by the different signal intensities of the single image points, which corresponds to a grey value or a brightness level within the MR image.

A known method which is currently used in a typical manner for performing attenuation and scattering correction of a PET image uses an additional computer-tomography (CT) image which is shot by means of a PET/CT scanner.

A CT image is generated by means of CT (computer tomograph), which represents another image-providing method, and the image is based on several X-ray recordings of a body section to be examined. These transmission recordings are computationally processed to form a three dimensional model so that arbitrary sectional images of the body section to be examined can be reconstructed. Different grey levels of the CT image correspond to differently attenuated signal intensities and provide insight into a density distribution of the body section, particularly into the arrangement of bones within the body section.

Attenuation values are determined from the CT image in a pointwise manner in order to perform attenuation and scattering correction based on the CT image, wherein the attenuation values are applied on the PET image in a pointwise manner.

One drawback of this method results from the radiation exposure of the organism examined. The organism is exposed to X-rays for the CT recording which if applied in heavy doses can lead to skinburns, cell mutation or similar.

Another method for performing an attenuation and scattering correction on a PET image is known from EP 1 105 750 B1.

The method explained there is based on a so-called "atlas registration" of the recorded PET image. An atlas is formed as a three dimensional computer model and contains two components, namely a functional component and an anatomic component. The functional component can be formed by CT, MR or PET images, and the anatomic component can be formed by transmission recordings (for example CT images).

The recorded PET image is "registered" with the functional component of the atlas, i.e. the PET image is aligned by comparison, particularly when applying a transformation, with the functional component of the atlas (in a special manner). The transformation applied to the recorded PET image, for that purpose, contains linear mappings (rotation, translation, scaling) as well as non-linear mappings for deforming the PET image. The determined transformation is applied to the anatomic component of the atlas for determining an attenuation map for the PET image therefrom.

One drawback of this method is to be seen in that the functional component of the atlas, particularly if formed by CT images, offers a bad contrast with respect to soft parts. The registration of the recorded PET image then happens by using the contours of bones which, in turn, are "fuzzy" or only badly recognizable in the PET image. Thereby, the alignment of the PET image in the atlas is complicated, so that the determined transformation is erroneous, and consequently, the attenuation map generated by using this transformation can only be insufficient for correcting the PET image.

Further, methods for correcting attenuation and scattering of γ-radiation applied to a PET image are known and performed on basis of MR images.

A known method which corrects a PET image based on an MR image is found on determining a point within the MR image corresponding to its spatial position for each interesting point of the PET image. Then, it is directly pointed to the attenuation and scattering value for the corresponding point of the MR image, which is then applied to the interesting point of the PET image, in order to allow correction of the interesting point by calculation.

A point of a PET or MR image designates a pixel in this context which is the base unit of a two-dimensional image, or a voxel, that is a three-dimensional equivalent of the pixel.

One drawback of this known method is that the assignment between an intensity of a point within the MR image and a correction value is not defined unambiguously. The point of the MR image does not contain sufficient information for deriving the morphological structure (bones, tissue, etc.), on which it is based, from its intensity alone, which determines the attenuation of the γ-radiation as well as multiple scattering processes occurring. Therefore, for example, it is possible that a point which images a bone is assigned to the attenuation value of air, since air and bones can be hardly differentiated in the MR image.

Another method for correcting a PET image based on an MR image calculates from the MR image a primitive attenuation map. For that purpose, it is differentiated between only two brightness levels in the MR image, and respectively one attenuation value is assigned to these brightness ranges. For example, within the MR image it can be differentiated between points located within the body and outside of the body. One drawback of this method is based on that information contained within the MR image related to the anatomy of the body is not considered upon the establishment of the attenuation map, so that the established attenuation map is not accurate. If this non-accurate attenuation map is applied to the PET image for correction purposes, hence the corrected PET image is not precise either.

Further, a method as well as a device for determining an attenuation map for a PET image based on an MR image is known from US 2006/0058641 A1. With this method a so-called MR atlas is used which is formed as a normalized three-dimensional model having attenuation maps deposited. The recorded MR image is registered with the MR atlas by means of a transformation in terms of a linear mapping (rotation, translation, scaling) so that the spatial position of the MR image within the MR atlas is determined by comparison. Thereby, the recorded MR image is adapted to the normalized three-dimensional model by the determined transformation. This transformation is applied to the associated attenuation map so that the attenuation map results for the recorded PET image.

This method has proven particularly disadvantageously if the recorded body section has untypical anomalies, such as arm lengths, sizes of organs or similar deviating from the standard, since they are not present in the MR atlas which is generated based on images of reference people. Thereby, registration of the MR image with the MR atlas is made difficult. Often, this results in heavily erroneous registrations. If this insufficient transformation is applied to the deposited attenuation maps of the MR atlas, this results in erroneous attenuation maps for the non-corrected PET image.

SUMMARY OF THE INVENTION

Therefore, there is still a need for an improved method of determining a property map, particularly an attenuation map, of an object based on at least a first image, particularly an MR image, which predicts in a very simple manner the property map with high precision and simultaneously without errors.

In accordance with the present invention this object with respect to the method as mentioned at the outset is solved in that a structure for a reference pair is defined, wherein each reference pair has at least two entries, wherein the first entry represents a property value, particularly an attenuation value, and wherein the second entry represents a group of associated image points belonging together which are particularly extracted from MR images, the image points including at least one interesting image point corresponding to the property value by additionally providing a plurality of training pairs, wherein a structure of the training pairs corresponds to the structure of the reference pairs, and wherein the entries of the respective training pairs are known, and by additionally determining an assignment between the first entries and the further entries of the training pairs by means of machine learning, thus allowing prediction of a corresponding property value for an arbitrary point of the first image. The means for defining a structure of reference pairs and providing a plurality of training pairs may be a computer system connected to an imaging system and equivalents thereof.

With the method of the present invention an approach for determining the property map of an object based on at least a first image is selected. In accordance with the invention, the property map, particularly the attenuation map, is determined by machine learning methods, particularly by classification and regression. By means of a support-vector machine an assignment, for example by using training data, between known property values (i.e. a first entry) and other known information, in terms of second and/or other entries, is determined. The once learnt assignment can thus be applied onto arbitrary points of the object, the property values of which are known in order to predict the corresponding property values. Thereby, the prediction can be performed particularly fast in an advantageous manner, since it has only to be reverted to knowledge already learnt and other steps for determining the unknown property values do not need to be performed.

Another advantage of the method of the present invention is to be seen in that the determination of the property map can be performed very accurately, namely in dependence on the number of training samples and the information considered during the machine-learning process. Particularly, the determination of the property map for a certain image is reproducible.

With a preferred embodiment, the structure of the reference pair additionally comprises a third entry which is considered during the determination of the assignment to the first entry together with the second entry. The means for providing the third entry may include a computer system connected to an imaging system and equivalents thereof.

This measure is advantageous in that an additional (source of) information is provided which is taken into account during the machine-learning process. Thereby, the accuracy of the assignment rule to be learnt is improved significantly, since complex contexts between the entries can be learnt for the purpose of recognizing and processing.

With another preferred embodiment, the third entry represents: a registered coordinate; another group of image points belonging together of at least a second image, wherein the other group of image points of the at least second image shows at least partially an identical object patch as the group of the image points of the first image; and/or a class affiliation.

This measure provides, in an advantageous manner, different information for the third entry of the structure of the reference pairs which are used individually as well as combined in dependence on desired goals for the assignment when learning and applying the assignment, in order to improve the assignment accuracy.

A "registered coordinate" is obtained in that the at least first (given) image is registered with a reference image. For this purpose, a linear mapping (translation, rotation, scaling) and/or a non-linear mapping (deformation) is determined which assigns to each point in the given image a point within the reference image. The "registered coordinate" of a point within the given image is the coordinate of the assigned image point within the reference image. The registered coordinate is indicated relative to a coordinate system which depends on the reference image. In this context, the coordinate system of the reference system does not necessarily have to be a Cartesian coordinate system. Particularly, an inhomogeneous density of the grid lines of the coordinate system is possible, wherein the density can be determined in dependence on location from certain properties of the reference image at this position.

With a particular embodiment several reference images can be used as well. The registration happens by means of a known algorithm (cf. e.g., "A survey of medical image registration", J. B. Antoine Maintz and Max Viergever, Medical Image Analysis (1998), Volume 2, number 1, page 136). Alternatively, the registration can be performed based only on surfaces as well, as disclosed for example by B. Schölkopf, F. Steinke and V. Blanz in "Object correspondence as a machine learing problem", Proceedings of the $22^{nd}$ International Conference on Machine Learing, 777-784, (Eds.) L. De Raedt, S. Wrobel, ACM Press, 2005. Also the registered coordinate as additional information can significantly increase the accuracy of the prediction at smaller errors with the registration, as they usually occur.

With another preferred embodiment required distances between registered coordinates are determined by means of a distance measure dependent on the position within the reference object, and not with a Euclidian distance as usual.

Many methods of machine learning determine implicitly the similarity between different input entries. The utilization of a position-dependent distance measure has the advantage that the weighting can be set differently within the used similarity measure in a position-dependent manner. Thus, the prediction emphasizes the registered coordinates more in regions within which the registration typically is performed without errors (e.g. within the skull) than in regions within which errors occur more often (e.g. within the stomach).

With another preferred embodiment the registered coordinates indicate the distances of the point corresponding to the interesting image point within the reference image relative to anatomically characteristic points to be determined.

This is advantageous in that the characteristic points can be found reliably. In total, the accuracy of prediction is increased.

The utilization of different groups of image points having different recording conditions increases the accuracy of learning the assignment in an advantageous manner so that consequently the prediction of an unknown property value is increased.

The utilization of a class affiliation allows the learning of the assignment not only based on properties of the groups of image points, but addition information on properties of the object to be examined are taken into account.

With another preferred embodiment the at least second image is a positron emission tomography (PET) image, or another MR image. Particularly, if one or more PET images are used, a point in time of the PET recording after injection of a tracer as well as properties and amount of the tracer can be used as additional entry into the structure.

This measure is advantageous in that, particularly during the determination of an attenuation map for a PET image based on an MR image, the reference pairs comprise other groups of image points additionally to the groups of image points from the MR images, which were recorded under the same conditions as the two pictures provided. Thus, additional images having other recording conditions or information by means of other examination methods do not have to be provided. Particularly, the MR images can have a $T_1$ weighting or a $T_2$ weighting so that the combined information can be considered as input during machine learning.

With another preferred embodiment the class affiliation includes: patient's age, patient's sex, patient's weight and/or patient's living habit.

This measure is advantageous in that information on patients can be considered during learning and applying an assignment in the field of medical picture processing.

With another preferred embodiment the group of image points belonging together preferably defines a rectangular window.

This measure is advantageous in that the group of image points form a connected region which can be selected easily and the properties of which can be considered during machine learning. The dimensions of the window can be chosen, dependent on the aim, freely or computer-based, by means of a computer program for "model selection".

With another preferred embodiment a subgroup is selected from the group of image points belonging together comprising the interesting image point.

This measure is advantageous in that not only area properties of the group are taken into account during learning, but also such which result from a line as well as from rings/spherical shells around the interesting point.

With another preferred embodiment each image point has an intensity value.

This measure is advantageous in that the intensity value represents a very simple information which can be considered with the machine learning process. The intensity value of an image point in case of an MR image can be, for example, a brightness level/grey value which can be determined from the MR image in a simple manner.

With another preferred embodiment a texture is determined for each group of image points belonging together.

A "texture" of a group of image points is to be understood, for example, as an intensity distribution (brightness levels/grey values) of the image points, from which the contours or similar—in dependence on the size of the group—can be recognizable. The machine learning of the assignment as well as application thereof based on the texture of the group represents another information in an advantageous manner, which can be considered with the method according to the present invention.

With another preferred embodiment an intensity histogram is established based on the subgroup, the histogram can be added to the structure as another entry.

This measure is advantageous in that another (source of) information for the machine learning process is provided. The intensity histogram indicates the intensity distribution of the image points with respect to the subgroup.

With another preferred embodiment an intensity average is formed based on the intensity values of at least the image points of the group of image points belonging together, the intensity average can be added to the structure as another entry together with the intensity of the interesting image point.

This measure is advantageous in that a still further (source of) information for the machine learning process is provided, in order to increase the assignment accuracy. The utilization of the intensity average of the group of image points or of the entire image, relative to the intensity value of the interesting image point can consider, for example, image-dependent properties which are caused by the image recording process.

With another preferred embodiment the at least first image, the MR images and/or the at least second image are preprocessed, particularly by wavelet transformation, Fourier transformation, SIFT, edge detectors or contrast amplification.

This measure is advantageous in that process steps for extracting features are applied to the at least first image, the MR images, the at least second image or also to the group of image points which are formed from this images. By means of this method, for example, the image contrast can be intensified, and individual image features can be worked out better.

With another preferred embodiment the second and additional entries of the data structure are fed into a method for reducing dimensions, particularly into an analysis of main components or a code book, the newly gained data description of which is added to the data structure as another entry, and also used for the prediction.

This is advantageous in that the entries are summarized in a compact manner and characteristic features are emphasized for this problem. In total, the speed of prediction of the property map can thus be increased.

With another preferred embodiment a structure corresponding to the structure of the reference pairs is provided for the arbitrary point of the object, and the structure of the arbitrary point comprises at least one entry different from the known first entry, wherein the first entry is missing.

This measure is advantageous in that the same structure as for the reference pairs is provided for the arbitrary point, the property value of which is unknown, so that the structure of the arbitrary point can be used as entry for the machine learning process.

With another preferred embodiment the prediction of the first entry of the arbitrary point is performed by applying the learnt assignment, based on at least one or more of the known entries of the arbitrary point.

This measure allows in an advantageous manner a fast and accurate prediction of the unknown property value, i.e. the first entry, of the arbitrary point based on one or more known entries.

With another preferred embodiment the prediction is performed substantially based on the second entries.

This measure is advantageous in that the group of image points of the arbitrary point as well as the properties determined therefrom represent an important source of information for predicting the unknown property value of the arbitrary point.

With another preferred embodiment the prediction is performed if a second entry is not known for the arbitrary point, based on one or more known entries.

This measure is advantageous in that, if the information on the group of image points is missing, the property value can nevertheless be predicted in a fast and accurate manner, since the other known entries represent an independent additional source of information with respect to the second entry.

With another preferred embodiment the prediction occurs, if the third entry of the structure represents a registered coordinate, in additional manner based on the registered coordinate.

This measure is advantageous in that a combined information of the second entry and the third entry in terms of the registered coordinate allows an accurate and reliable prediction of the unknown property value.

With another preferred embodiment the at least second image is additionally used for registering with the at least first image, and for extending the at least first image.

This measure is advantageous in that still another (source of) information can be used for predicting the first entry of the arbitrary point of the at least first image. This information is provided by the already recorded second image so that neither additional images nor other information due to other methods is have to be provided.

This extension of the at least first image is particularly advantageous if the at least first image shows a smaller patch of the at least second image. For example, this occurs with an MR thorax recording of a human being, since the additionally recorded PET image is recorded including arms put on, whereas the MR image is recorded when the arms are stretched over the head in an axial direction. Although the MR image shows a smaller patch, then the property map, i.e. the attenuation map, can be provided for the entire PET image. Thereby, recording artefacts within the MR image can be balanced out additionally, since the erroneous region of the MR image can be extended based on the registration with the PET image.

BRIEF DESCRIPTION OF THE DRAWINGS

Additional advantages and features result from the description following hereinafter and the accompanying drawings.

It is clear that the features mentioned above and to be explained below cannot only be used in the given combinations but also in other combinations or alone, without departing from the scope of the present invention.

Figure 1:
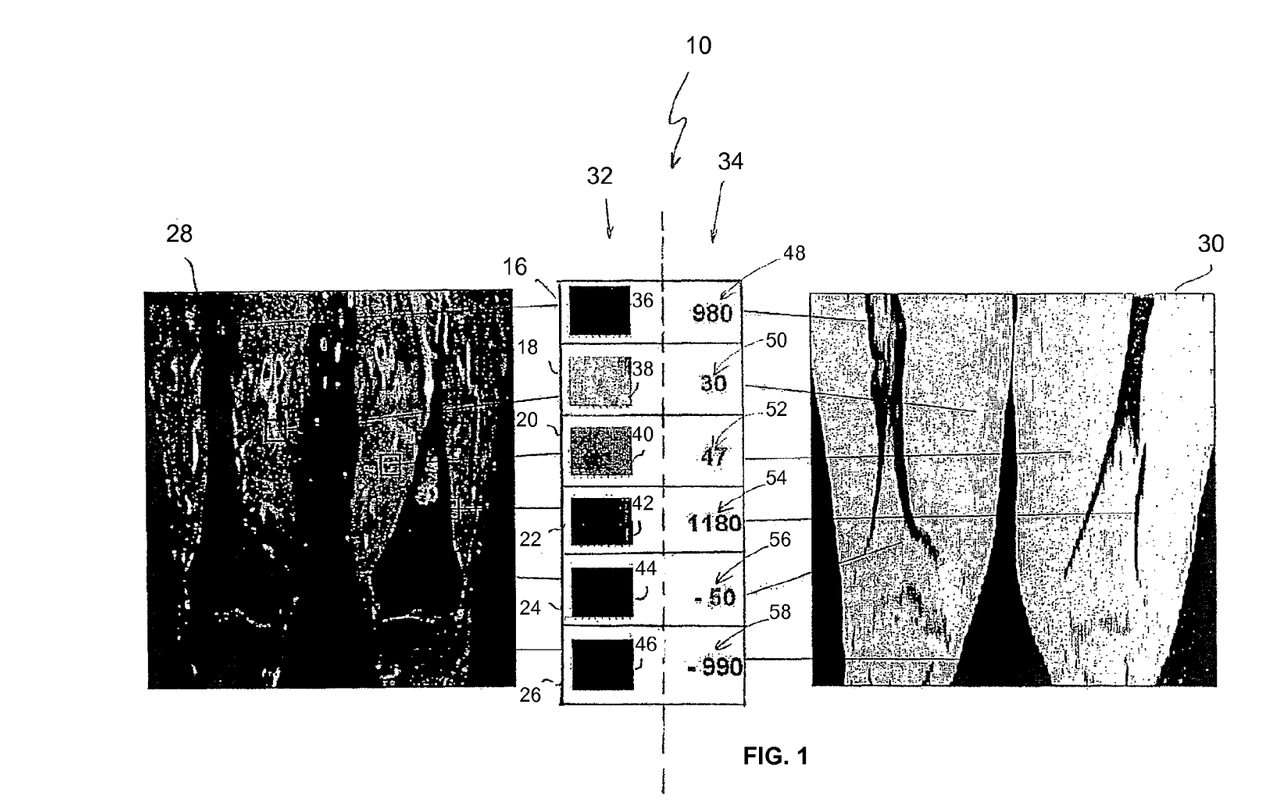
FIG. 1 shows a schematic illustration of a training example of a learn machine including an MR image and a corresponding attenuation map.

The invention will be described and explained in more detail by using some selected embodiments in the context of the accompanying drawings, in which:

FIG. 1 illustrates a training example which is designated generally with reference numeral 10, which is used with a method 12 for determining a property map of an object based on at least a first image.

PREFERRED EMBODIMENTS OF THE INVENTION

The method is used, for example, in processing medical images for determining an attenuation map in order to correct a PET image of a living being based on an MR image. Two recording effects of the PET image, i.e. attenuation as well as scattering of gamma radiation occurring during positron/electron annihilation, are to be corrected in a quantitative manner at least partially by means of the method.

Generally, the method of the invention is used for determining a property map of an object. Alternatively, probabilities for the property value can also be calculated for each interesting point besides a property value, namely for all points. With the method of the invention machine-learning methods are used for learning first—in a pointwise manner—for different image points of an image an assignment between a property value (output) and different information (input), i.e. an assignment rule is learnt from the input to the output. At a later time, the learnt assignment is applied to an arbitrary point of an unknown, i.e. non-learnt, (patient) image, in order to determine an unknown property value of the point based on information of this point, i.e. information corresponding to the inputs.

For example, an assignment between MR images and an attenuation value is learnt, wherein the attenuation value can be represented by a CT image corresponding to an MR image. If the assignment "MR image/CT image" is learnt, a CT image can be calculated based on an MR image of a patient, although a CT image has not been recorded. Then, this information can again be used for correcting attenuation of a PET image. Alternatively, other properties such as a differentiation between tumour tissue and healthy tissue, an identification of organs contained within the picture, tissue and bones, a differentiation between locations within and outside of the patient's body, and similar things can be learnt as well. Such properties are also called "labels".

In accordance with the present invention first a structure of reference pairs is defined. In this context, each reference pair comprises at least two entries. A first entry of each of the reference pairs represents the property value (label), i.e. the output, and the other entry represents the inputs (sources of information) for the purpose of machine learning. Particularly, the second entry represents a group ("patch") of image points belonging together including an interesting image point. The interesting image point is the point which is selected for determining its properties. In a simple case, the group of image points is represented by a window which has the interesting point preferably in its (geometrical) centre. The second entry is preferably provided from images recorded under identical modalities (e.g. same image-providing method, same field-of-view, etc.) like the patient's image to be processed later.

Further, a plurality of training pairs, i.e. images having known properties, is provided, the structure of which corresponds to the structure of the reference pairs. A recording modality of the images, from which the training pairs are preferably extracted, corresponds to the recording modality of the first image. The entries of the training pairs are known so that an assignment between the input and the output of the training pairs can be learnt by means of machine learning. After the assignment is learnt, at least some of the training pairs become actually reference pairs, which is unproblematic due to the same structure. The means for defining a structure of reference pairs and providing a plurality of training pairs may be a computer system connected to an imaging system and equivalents thereof.

Further, the assignment learnt can be applied to an arbitrary image point of a patient's picture, some more information, such as its intensity, are known, but the output of which, such as its property value, is unknown. In this context, the structure of the arbitrary point should correspond to the structure of the reference pairs, i.e. if an attenuation value for a group of points (patch) has been learnt with the reference pairs, then the (unknown) interesting point should be embedded into a corresponding group for allowing application of the learnt assignment onto the unknown point. The machine learning process generally is founded on pattern recognition and is performed by a learning machine, preferably by a support-vector machine as exemplarily described in B. Schölkopf and A. J. Smola, "Learning with Kernels", MIT Press, Cambridge, Mass., 2002. The machine learning represents a complex process, and alternatively comprises support-vector regression, Gaussian processes, Method of k-Nearest-Neighbour, regression/classification trees or similar.

Speaking with very simplified and pictorial words, the prediction of the unknown property value (respectively the application of the learnt assignment) of an arbitrary point within the patient's image is founded on comparison of the input of the arbitrary image point with inputs of the reference pairs so that, for example, a best-matching input is selected from the inputs of the reference pairs. The arbitrary point can then be assigned to with the property value of the reference pair, the point having this best-matching input. Of course, the actual prediction is significantly more complex, mainly as complex as the machine learning process itself. The property value is actually calculated. However, it appears that the metaphor of comparing a list of reference pairs including a subsequent selection of a best pair is relatively illustrative. Examples given hereinafter merely serve for facilitating illustration, and therefore are not intended to be limiting at all.

Returning to the method in accordance with the invention, groups of image points of the images used, i.e. individual partial regions as well as the entire images can be pre-processed by image-processing steps, such as Fourier transformation, SIFT, edge detectors, contrast amplification or similar, for improving the pattern extraction. This applies to both the learning from known images and the later application to unknown images.

The second entry, i.e. the group of image points belonging together define a window preferably rectangular window which comprises the interesting image point, the property value of which is to be learnt. However, the window might also be circular or have an arbitrarily defined border. Preferably, the window comprises, besides the interesting point, at least another point, particularly a direct neighbour. Generally, the group of points belonging together, however, does not need to consist of points linked up. Dimension of the window can be selected independent on a desired target. It can be selected by means of a computer program for model selection. The window dimension can affect the accuracy and calculation time of the method of the invention. For example, if the images are defined by raster-like arranged points, e.g. pixel (two-dimensional base unit of two-dimensional images) or voxel (three-dimensional base unit of three-dimensional image), the window can be formed quadratic or rectangular in case of pixels, and cubic or ashlar-like in case of voxels. Side lengths of the window can comprise values in the range of millimeters or centimeters so that the group of image points can represent an entire image or patch of an image as well. Further, it is possible to arrange the interesting point centrally within the window, or the point can be displaced from the centre point of the window. The dimension is preferably defined in the order of image points.

Referring to FIG. 1, in the left-hand part of the Figure exemplarily an MR image of thighs, in the middle a "list" of reference pairs or training pairs and in the right-hand part an attenuation map is shown corresponding to the left-hand image. The training example 10 for the learning machine shown in FIG. 1 comprises six training pairs 16-26. The training example 10 comprises an MR image 28 and the attenuation map 30 corresponding to the MR image 28, which here exemplarily is a CT image. The images 28 and 30 have been recorded of the same person, preferably without displacement of the person between the recordings, and preferably at the same field of view.

An assignment is learnt from an input 32 to an output 34 by means of the training example 10. In FIG. 1, the inputs are respectively shown at the left hand side and the outputs are respectively shown at the right hand side at the training pairs 16-26, which are illustrated for illustration purposes separated by a broken line. The inputs 32 respectively represent the second entry of the structure of the training pairs 16-26 in terms of six windows 36-46, here having a rectangular shape and being extracted from the MR image 28. Further, attenuation values 48-58 are provided which are extracted, for example, from the CT image 30.

In more detail, this means that the points within the MR image 28 are selected, a window is defined around the selected points, this window is "cut out", and an attenuation value is assigned thereto. The attenuation value is obtained by searching in the CT image 30 (metrically) for that point which corresponds in the MR image 28 to the selected point, and then extracting the attenuation value of the point found in this manner in the CT image 30. In this manner a plurality of training pairs 16-26 can be formed which are required for subsequently determining an assignment between the inputs 32 and the outputs 34.

Assigning the window 36-46 to the known attenuation values 48-58 belonging thereto is determined by means of machine learning. The training pairs 16-26 are respectively formed by a window 36-46 and an attenuation value 48-58, which are later used as reference pairs 16-26 for predicting an unknown attenuation value of a new window. The training pairs and reference pairs are, in this term, identical. In practice, the learnt assignment is then applied to an unknown point within the image for determining its (unknown) property value belonging thereto by calculation. An actual comparison with the reference pairs does not occur. Insofar the terms "training pairs" and "reference pairs" are synonym and merely used for simplification of explanation and understanding.

With (machine) learning the assignment from the input 32 to the output 34 characteristic features of the windows 36-46 can be used, such as an intensity distribution. In the MR image 28 the intensity of an image point corresponds to a brightness level/grey value. The window 38 shows a rectangular image patch of the person's right thigh containing a thigh muscle. The intensity distribution within the window 38 allows recognition of a lighter partial region extending diagonally from the upper left to the lower right which is considered during learning the assignment of the corresponding attenuation value 50. Further, the window 42 shows the thigh muscle and a thigh bone so that the intensity distribution of the window 42 comprises two regions being vertically separated from each other, a first region being light and a second region being dark. The light region shows the muscle, and the dark region shows the bone. The window size here is dimensioned so that both the bone and the muscle adjacent thereto can be recognized so that this feature is considered when learning and applying the assignment, and erroneous prediction of an unknown attenuation value can be largely excluded. If the window 42, for example, would only comprise the dark region, a window similar to the window 42 could be assigned wrongly to an attenuation value of air, since air typically possesses a very dark intensity distribution. Therefore, "characteristic" pairs are preferably used, i.e. pairs, textures and similar of which can be recognized clearly.

Figure 2:
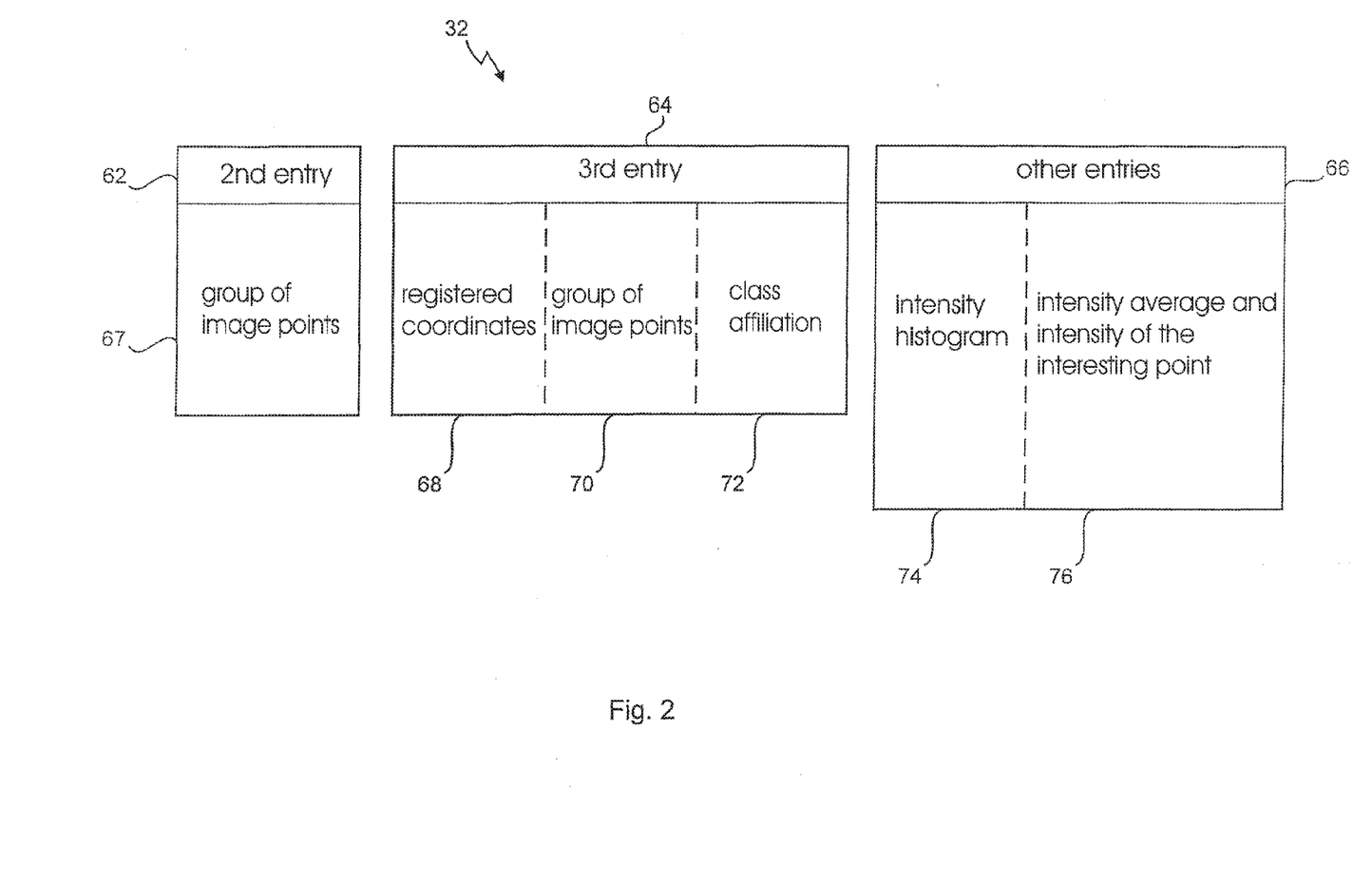
FIG. 2 shows a schematic illustration of an input to the learning machine.

Entries (sources of information) 62-66 are exemplarily shown in FIG. 2, which can be used as inputs 32 and can be considered when learning the assignment. The individual input 62-66 can be provided independently from each other, and are significant for the machine learning in the same way. The second entry 62 comprises a group 67 of image points belonging together, which comprises an image point which is actually interesting. As explained above, the group of image points defines the window.

Here, each image point comprises an intensity so that a "texture" can be determined for each group of image points. The texture of the group of image points means, for example, an intensity distribution (brightness levels/grey values) of the image points, from which —in dependence on the size of the group—contours or similar can be recognized. Both the intensity of the interesting image point and the intensity distribution of the window is taken into account when determining (and applying) the assignment.

A third entry 64 (of the input 32) represents, among other things, registered coordinates 68, another group of image points 70 belonging together, and/or a class affiliation 72, which can be combined individually as well as with each other. The third entry 64 also represents a plurality of additional sources of information which can be re-accessed. The examples mentioned here are not concluding. It is clear that several additional sources of information can be taken into account simultaneously. In this case, also fourth, fifth, sixth, etc. entries were to be added, which will be explained in a summarized manner under the third entry 64 here in FIG. 3.

A "registered coordinate" is obtained by registering at least first image and, if necessary, additional images with one or more reference images, which have been recorded under the same modalities. For that purpose, a linear mapping (translation, rotation, scaling) and/or a non-linear mapping is determined which assigns to each point of the at least first image a point within the reference image. The "registered coordinate" of a point within the given image is the coordinate of the assigned image point within the reference image. The registered coordinate is given with respect to a coordinate system which is dependent on the reference image. As an alternative to the generally three-dimensional coordinate system, the position of the point within the reference image corresponding to the interesting point can also described relative to the anatomic characteristic position within the reference image, such as the nose tip.

With a particular embodiment of the present method also several reference images can be used, particularly, for example, different reference images for different sexes or different classes of age can be used. Also, separate reference images can be used for different anatomical sections.

Even with smaller errors during the registration—as they might happen—the registered coordinate, as additional information, can significantly increase the accuracy of the prediction. For example, since air and bones have the same intensity within an MR image, and the attenuation value thereof (high for bones, low for air) cannot be determined unambiguously, often an inaccurate local information helps: within the lung rather air is assumed, in the vicinity of the skull bones are assumed.

A registered coordinate can also be determined outside of the given image, since the transformation, mapping the given image onto the reference image, can be continued steadily (for example, linear transformations are replicable within the entire space).

The information on the local position of the image points increases the accuracy during an assignment so that wrong learning or applying of the assignment at least can be minimized or completely excluded. Thus, it is, for example, important to know where the arbitrary point is roughly located. For example, if the smallest finger of the left hand is viewed (in the known image), then it is certainly located within the bigger (spatial) area of the left hand. This (rough) information can also be extremely important for the learning machine and a later application of the learnt assignment, particularly if comparable (with the finger) reference pairs exist which, however, have been extracted, for example, from images of the feet. The registered coordinate thus represents another source of information for determining a property value of an image point from an (unknown) image, which is of great help.

Another group of image points 70 can be provided from other images which have been recorded either under the same or different recording modalities, from which the group 67 of image points of the second entry 62 has been extracted. Further, the additional image comprises (at least partially) an identical patch of the object like the group of image points of the first image.

The other group of image points, for example, represents another window, image patch or a complete image. For example, the second image—with a method for determining the attenuation map of an MR image (first image) based on a PET image—can be another MR image or PET image, particularly the non-corrected PET image. The other MR image, for example, can have another weighting as the first image ($T_1$ and $T_2$ weighting of MR images) so that another information for the machine learning is present.

The second image can be used additionally for registering the first image with the second image. This is of particular advantage if the first image, such as an MR image, comprises geometrical distortions as they frequently occur in MR images, which is technically caused. If the second image is geometrically precise, the geometrical distortions of the first image thus can be corrected easily. The second image can be used as an additional extension to the first image. This is particularly advantageous if the first image shows a smaller image patch than the second image. In this case, prediction outside of the image patch of the first image can only be performed on the basis of information of second image property value, particularly attenuation value, for the missing region of the first image. Also, class affiliation 72 can be a third entry 64. The class affiliation can comprise other properties of the object, in dependence on the object. If the object is, for example, a patient, hence it comprises e.g. a patient's age, a patient's sex, a patient's weight and/or a patient's habit, such as smoking.

Additional entries 66 of the input 32 comprise an intensity histogram 74 and/or a property of the image point with respect to the group of image points 67, 76 such as an intensity value of the interesting image point relative to an intensity average of a partial region of the image or with respect to the entire image.

The intensity histogram 74 can also be formed from an intensity distribution of a subgroup of the group of image points 67, 76 belonging together, which comprise the interesting image point. For example, the subgroup can be selected in terms of a line, or also as a ring or a spherical shell. The intensity histogram represents, for example, the intensity distribution in dependence on the distance relative to the interesting image point of the subgroup.

An intensity average is formed for the additional entry 66 of the input 32 based on the intensity value of the group of image points, i.e. the window, the image patch, or the entire image, the intensity average being added to the input 32 together with the intensity of the interesting image point.

The second, third and additional entries can comprise, among other things, a lot of different information, which, however, partially can be quite similar with respect to each other. Therefore, groups of entries, which are particularly similar with respect to each other, can also be found by using the training pairs, instead of storing all the entries. Then, it is sufficient to merely save an index of the group instead of all the individual entries. Hence, these indexes are informative in exactly the same way with respect to the assignment, however this can be performed much faster and more precisely. These methods are known under the terms dimensional reduction method, particularly analysis of main component or codebook. In a preferred implementation of the described method the entries calculated for the training and reference pairs as well as for those pairs, the property values of which are to be determined, are compressed by the aid of this method. From a formal point of view, compressed entries are calculated, and these are added to the structure as an additional entry. The learning algorithm can then, under certain circumstances, merely consider this new entry for an assignment.

The prediction of the unknown property value of the arbitrary point of the first image thus is performed based on one or more known entries of the arbitrary point. Spoken in pictorial words, if the predicting is performed by comparing the known entries (for example intensity/pattern within the window) of the arbitrary point with the entries of the reference pairs, then, if several inputs of different reference pairs correspond similarly good to an entry of the arbitrary point, the number of these similarly good reference pairs can be reduced based on the other known entries of the arbitrary point for determining the correct property value.

The prediction of the unknown property value of the arbitrary point can be based substantially on the second entries 62. In this context, the intensity of the point/image point as well as the texture of the group of image points is taken into account. If the third entries 64 represent the register coordinate 68, then they can be taken into account when predicting the unknown property value, in order to increase the accuracy of assignment. If the arbitrary point (having an unknown property) does not comprise a second entry 62, then the prediction of the unknown property value of the arbitrary point is performed based on one or more of the known entries 64, 66 of the arbitrary point.

Figure 3:
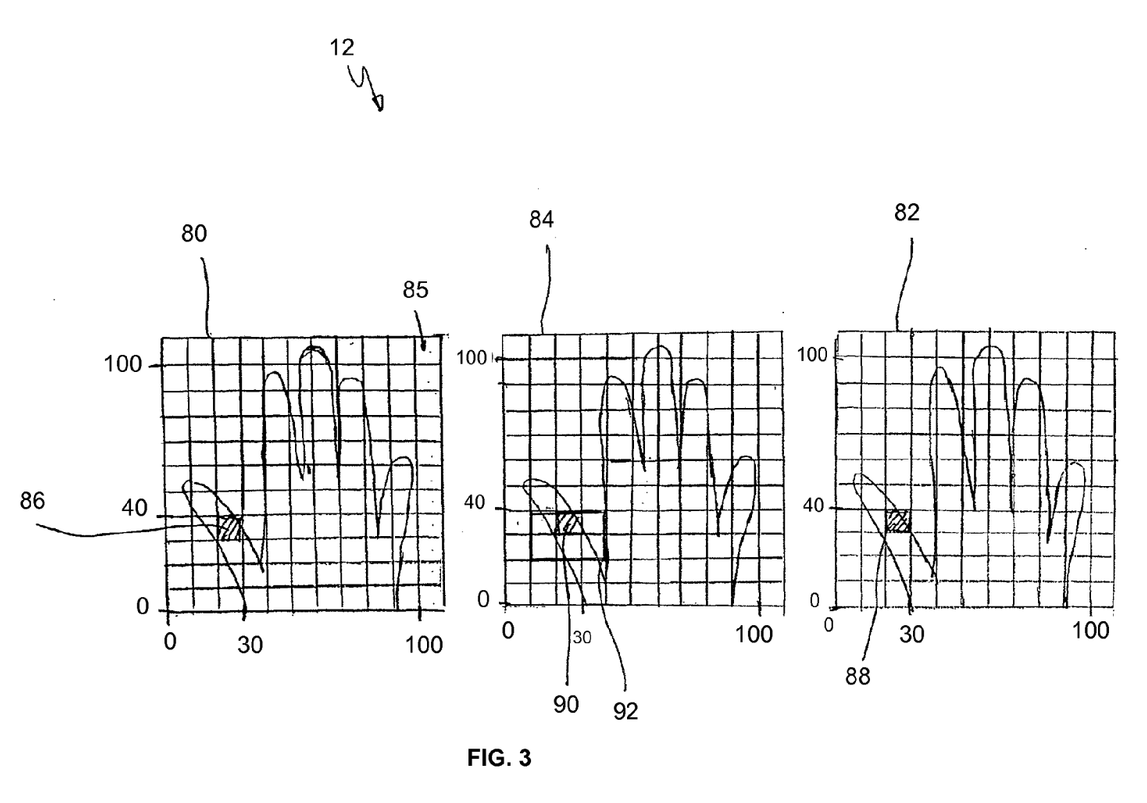
FIG. 3 shows a schematic illustration of a PET image, a corresponding MR image and an associated attenuation map.

In FIG. 3, the method 12 is illustrated exemplarily for a non-corrected PET image 80, the attenuation map 82 thereof is to be determined based on an MR image 84. The PET image 80 and the MR image 84 are provided, for example, by a PET/MR scanner and show recordings of a left hand of a smoking patient being 40 years old. These (in this example only) two-dimensional images 80, 84 are defined by pixels being schematically indicated by generally rectangular points 85, which here are coarse and in practice are significantly finer. A corresponding attenuation value (numerical value) 88 for a specific pixel 86 of the PET image 80 is to be determined by means of the method of the invention. For that purpose, a pixel 90, which corresponds to the pixel 86 of the PET image 80 with respect to its spatial position, is selected from the MR image 84, and a window 92 is determined around this pixel 90. The window 92 comprises, besides the pixel 90, five other pixels directly neighboring. The window 92 represents the second entry 62 (cf. FIG. 2) of the input 32 (cf. FIG. 1) for the learning machine. For example, the registered coordinate 68 of the pixel 90 can be used as a third entry 64 of the input 32, the registered coordinate corresponding to the pair of values (30/40) in this example. In this context, the MR image 84 has been registered with a reference image, i.e. the MR image 84 has been aligned within the reference image by means of a transformation. The class affiliations of the patient, i.e. his sex (male), age (40 years) and habit (smoking), can be used as another entry 64. Thus, no training pairs/reference pairs are taken into account during the assignment, which have been gained based on, for example, a 60 year-old non-smoking female. Then, it can be exemplarily considered that bones are embrittling in the age, i.e. have a lower density, and, thus, result in a lower attenuation. The associated attenuation value 88 for the pixel 90 (or the pixel 86) can be predicted based on the entries of the pixel 90 by means of an assignment learnt by using the training pairs having identical structure. In the above-given picture, the prediction is founded on assigning (e.g. comparing) the input 32 of the pixel 90 to the entries of the reference pairs. By using the entries 62, 64 of the pixel 90 all reference pairs are selected, entries of which are similar to at least one entry 62, 64 of the pixel 90. Then, the best-matching reference pair is selected from these reference pairs, for the entries of which correspond to the entries of the pixel 90. The first entry of this reference pair is then assigned to the attenuation value of the pixel 88. In practice, the attenuation value is calculated by means of the learning machine, which is much more complex than the comparison being pictionary described here, and in general is not identical with a comparison.

If the attenuation map 82 is provided from CT images, it must be translated to the corresponding attenuation map for PET images, as described, for example, in P. E. Kinahan et al., "Attenuation correction for a combined 3D PET/CT scanner", Med. Phys. 25(19), 1998.

Figure 4A:
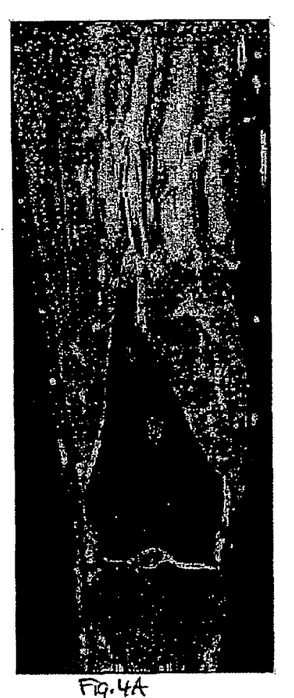
FIG. 4A shows a patch of the MR image of FIG. 1.
Figure 4B:
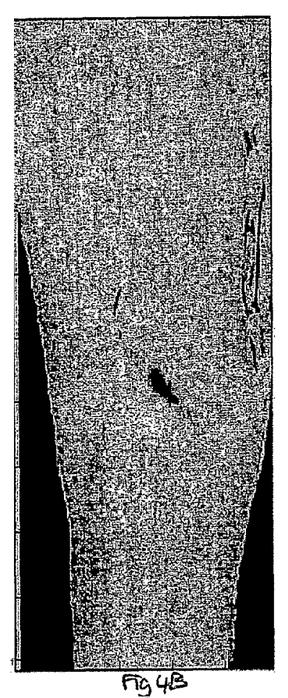
FIG. 4B shows an attenuation map of a PET image, showing the patch of FIG. 4A and which was calculated by the method in accordance with the present invention (without registered coordinates)
Figure 4C:
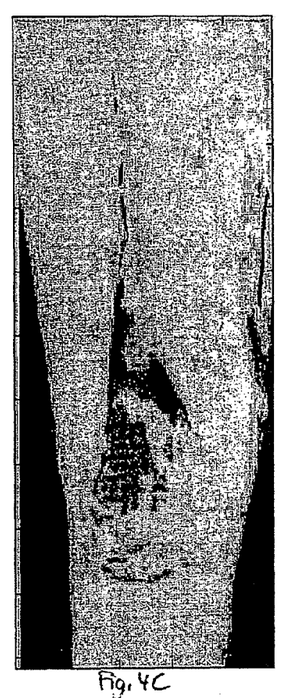
FIG. 4C shows another attenuation map of a PET image, the patch of which is shown in FIG. 4A and which was calculated by the method in accordance with the present invention (including registered coordinates)
Figure 4D:
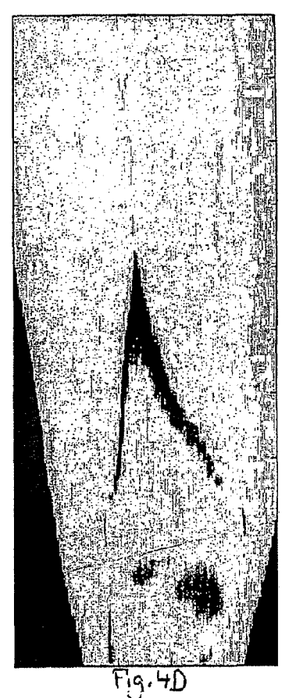
FIG. 4D shows an attenuation map of a PET image, the patch of which is shown in FIG. 4A.

FIGS. 4A-4D depict an example for the different accuracy of the method in accordance with the present invention based on the used information. FIG. 4A shows a patch of the MR image of FIG. 1 and thus presents a recorded MR image for which an attenuation map is to be learnt. If this attenuation map is provided by using windows, for example, by means of supported-vector regression (FIG. 4B), then it has a lower accuracy in comparison to an attenuation map which uses both windows and the registered coordinates (FIG. 4C). FIG. 4D shows, for comparing purposes, an attenuation map determined based on CT images.

Figure 5:
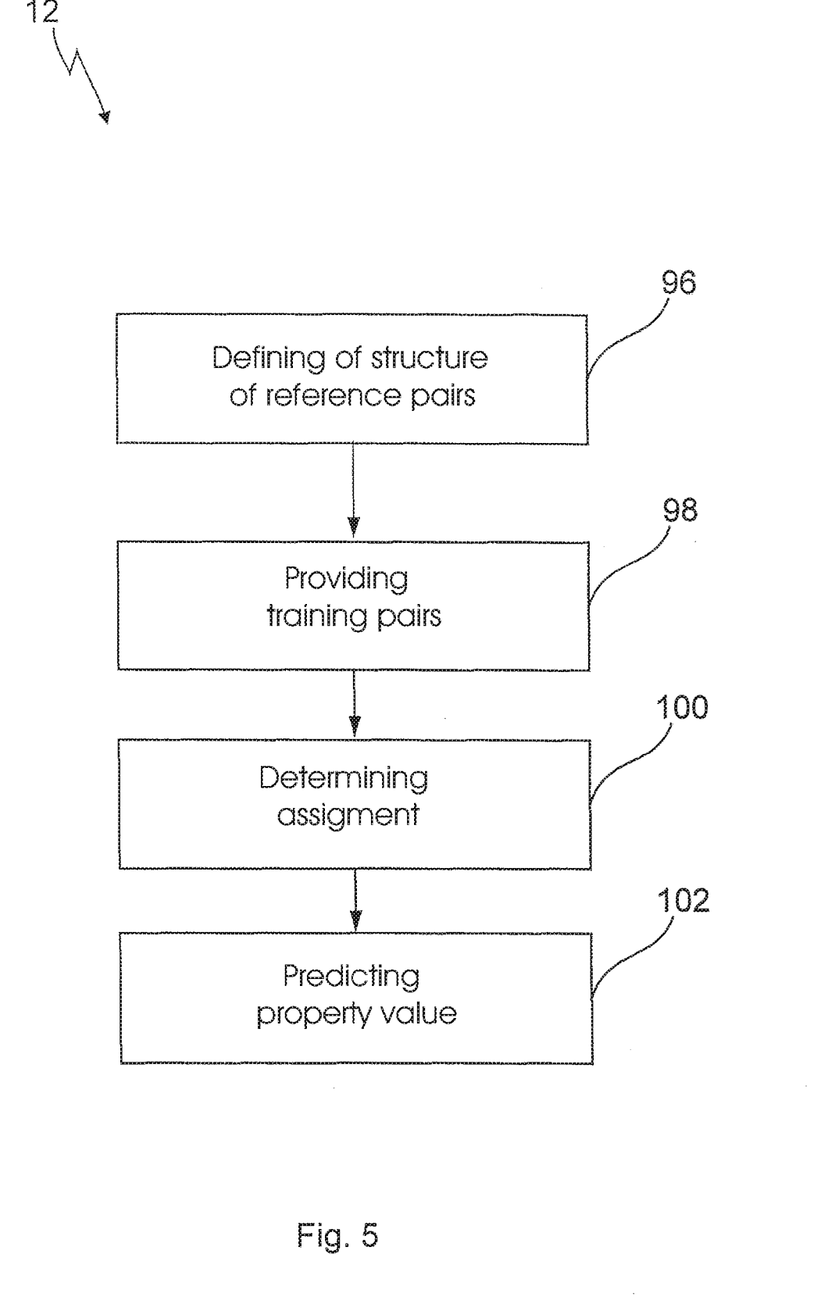
FIG. 5 shows a flow chart of a method in accordance with the present invention.

FIG. 5 shows a flow chart 94 of the method 12 in accordance with the invention. In a first method step 96, the structure of the reference pairs is defined, comprising input(s) and an output for the learning machine in terms of entries. In the next method step 98, a plurality of training pairs is provided, the structure of which corresponds to the structure of the reference pairs. The assignment between the input and the output of the training pairs is determined in another method step 100 by means of machine learning, then the assignment is applied to an arbitrary point in another method step 102, in order to predict the unknown property value of the arbitrary point based on the known entries of its input.

Figure 6:
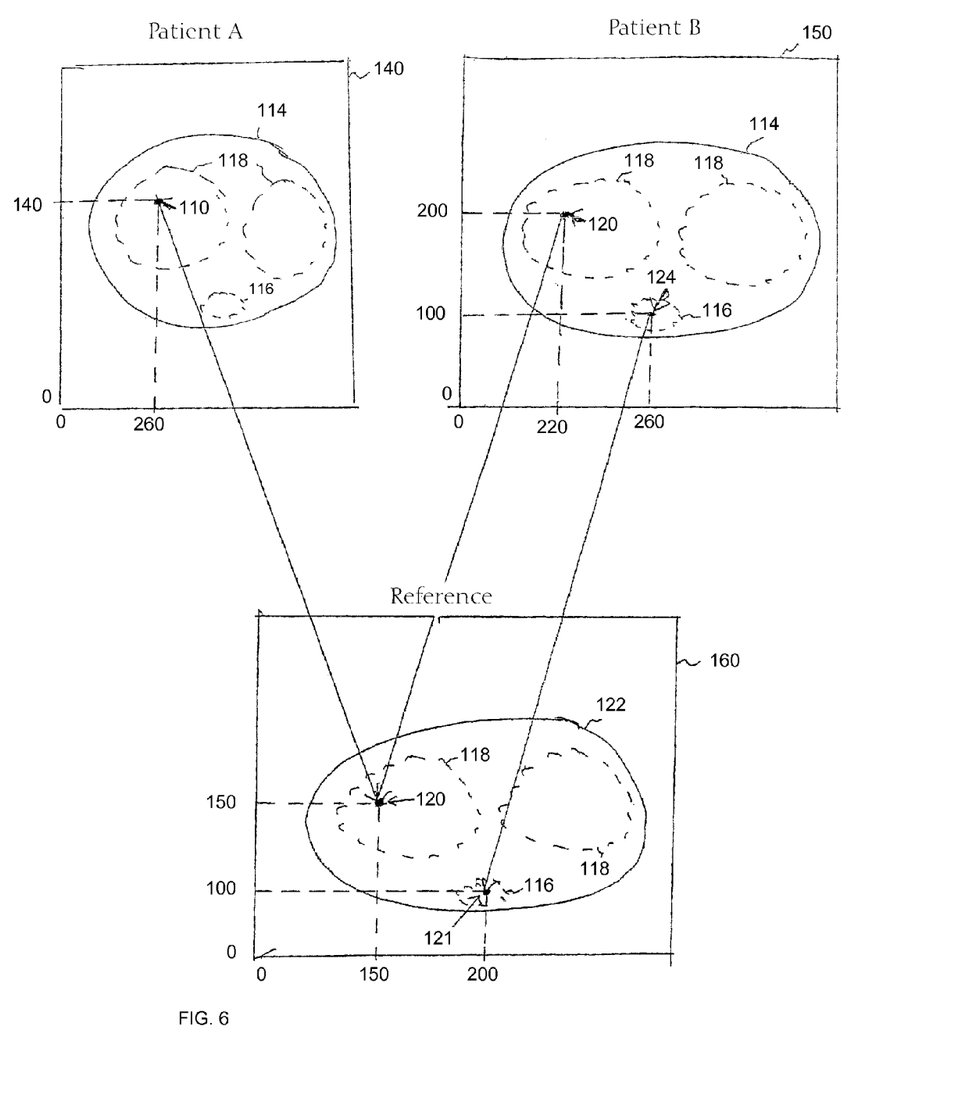

With reference to FIG. 6 operation with registered coordinates is once again shown in an exemplary manner.

Occasionally, neither the intensity of an individual interesting point nor a window around the interesting point contains sufficient information for determining a property value of the interesting point unambiguously. For example, one MR image point could be entirely dark, since it shows a point in air, or since the point is located entirely within a bone. Similar applies for a window around this point. Therefore, it can be necessary that the learning machine needs further input information. Here, registered coordinates can be of assistance.

In the upper half of FIG. 6 two images 140 and 150 are schematically shown, which respectively show a section through a patient's body (114) in the thorax region, wherein the patients are different and respectively the lung 111 and the spine 116 can be recognized. An (interesting) point 110 in the first image 140 is located centrally within the lung 118. Within the image 140 it has, for example, the coordinates 140/260. The anatomically corresponding point is the point 120 in the image 150 having the coordinates 200/220. In the lower half of FIG. 6 an image 160 of a "reference human being" 122 is shown.

It is assumed that the property map for the second image 150 and the training/reference pairs are known, which are gained therefrom. Particularly, two reference pairs are taken at the points 120 and 121. The window of both is dark, since air within the lung, and bones within the spine respectively do not generate a signal in the MR image; the associated property value, here for example a PET attenuation value, is, however, heavily different, i.e. high for bones and low for air.

If now the unknown attenuation value is to be determined for the point 110 in the image 140, then the second and other entries of the data structure are compared with the corresponding entries of the reference pairs for providing the prediction—simplified spoken—by using the most similar pair. Since both are dark, the window around the point 110 in the image 140 and the window of the reference pairs in the image 150, based on this information it cannot be decided which reference pair is more similar. If the coordinates of the interesting point 110 (140/160) in the first image 140 are directly compared with those of the reference pair at the position 120 (200/220) in the second image 150, then these, at first, are not particularly similar although they anatomically designate the same point. The selection of one of the two reference pairs by using these coordinates would be accidental and fail in the shown example, i.e. the point 121 having the coordinates (100/260) would be selected. Thereby, the predicted attenuation value (high) would be wrong.

By using the registered coordinate (150/150) for the interesting point, as well as correspondingly for the reference pairs (150/150) and (100/200), the assignment nevertheless becomes unambiguous. The reference pair at the position 120 has the same registered coordinates (150/150) like the interesting point 110, and thus is more similar than the second reference pair at location 121 having the registered coordinates (100/200). The predicted attenuation value (low) now is correct.

It is clear that the above explanations once again merely serve for a pictorial illustration and must not to be interpreted limitative.

Further, it is to be noted that for each interesting point the property value is determined by means of an atlas registration, and this value can be added to the structure as another entry.

This aspect makes the method of the present invention superior to the known atlas methods. With the known atlas methods the registered ordinate is only and solely responsible for the resulting attenuation value. The actual intensity is no longer of interest, since it is only required in a first step for "orientation" within the atlas, wherein not only one image point (including its intensity) but all image points of the image are required. If the image has anomalies, which are too significant, then in the prior art already the "orientation" within the atlas is unsuccessful. However, in accordance with the present invention anomalies do not present a problem.

Therefore, we claim:

1. A method for determining a property map of an object based on at least a first magnetic resonance (MR) image of the object, comprising:
    defining a structure of reference pairs, wherein each reference pair has at least first and second entries, wherein each of said first entries represents an unknown property value, and wherein each of said second entries represents a group of image points belonging together, which are extracted from said first MR image recorded by a scanner, wherein the group of image points includes at least one interesting image point which corresponds to one of the unknown property-values, wherein each unknown property value represents an attenuation value; providing a plurality of training pairs, wherein a structure of the training pairs corresponds to the structure of said reference pairs, and wherein first and second entries of the respective training pairs are known; and determining an assignment between the first entries and the second entries of the training pairs by machine learning, and predicting an attenuation value for an arbitrary image point which corresponds to the at least one interesting image point of the first MR image by applying the determined assignment to one of the second entries of the reference pairs including said arbitrary image point.

2. The method of claim 1, wherein the structure of said reference pairs additionally comprises third or additional entries, which are taken into account during the step of determining the assignment.

3. The method of claim 2, wherein the third or additional entries are selected from a group consisting of:
a registered coordinate;
another group of image points belonging together of at least a second image, wherein the other group of image points of the at least second image shows at least partially an identical object patch like the group of image points of the first image; and
a class affiliation.

4. The method of claim 3, wherein the registered coordinate is defined by one of a coordinate of a point equivalent to the interesting point in a reference object, and one or more distances of a point equivalent to the interesting point relative to anatomically characteristic positions within the reference object.

5. The method of claim 3, wherein a similarity between the registered coordinate and a position-dependent distance measure is determined, which is dependent on properties of a reference object as well as a position of an equivalent point within the reference object.

6. The method of claim 3, wherein the at least second image is one of a positron emission tomography (PET) image and another MR image recorded by a scanner.

7. The method of claim 3, wherein at least one of the at least first MR image and the at least second image are pre-processed by the extraction of features.

8. The method of claim 7, wherein the pre-processing is performed a Fourier/Wavelet transformation, SIFT, edge detectors, or contrast amplification.

9. The method of claim 3, wherein additionally at least the second image is used for registering with the at least first image, and for extending the at least first image.

10. The method of claim 1, wherein said second entries represent registered coordinates.

11. The method the claim 1, wherein the group of image points belonging together defines a window.

12. The method of claim 11, wherein the window is rectangular.

13. The method of claim 1, wherein a subgroup is selected from the group of image points belonging together, which comprises the interesting image point.

14. The method of claim 1, wherein each image point has an intensity value.

15. The method of claim 14, wherein an intensity histogram is established based on a subgroup, which can be added to the structure as another entry.

16. The method of claim 1, wherein a texture is determined for each group of image points belonging together.

17. The method of claim 1, wherein an intensity average is formed based on intensity values of at least the image points of the group of image points belonging together, the intensity average being added to the structure together with the intensity of the interesting image points as another entry.

18. A system for determining a property map of an object based on at least a first magnetic resonance (MR) image of the object, comprising:
an imaging system;
a computer system connected to the imaging system;
wherein the computer system is configured to execute a series of steps to determine the property map of the object, the steps comprising:
defining a structure of reference pairs, wherein each reference pair has at least first and second entries, wherein each of said first entries represents an unknown property value, and wherein each of said second entries represents a group of image points belonging together, which are extracted from said first MR image recorded by a scanner, wherein the group of image points includes at least one interesting image point which corresponds to one of the unknown property values, wherein each unknown property value represents an attenuation value;
providing a plurality of training pairs, wherein a structure of the training pairs corresponds to the structure of said reference pairs, and wherein first and second entries of the respective training pairs are known; and
determining an assignment between the first entries and the second entries of the training pairs by machine learning, and predicting an attenuation value for an arbitrary image point which corresponds to the at least one interesting image point of the first MR image by applying the determined assignment to one of the second entries of the reference pairs including said arbitrary image point.

19. A non-transitory computer readable medium comprising a set of instructions that when executed by a computer processor, result in a series of steps being performed to determine a property map of an object based on at least a first magnetic resonance (MR) image of the object, the steps comprising:
defining a structure of reference pairs, wherein each reference pair has at least first and second entries, wherein each of said first entries represents an unknown property value, and wherein each of said second entries represents a group of image points belonging together, which are extracted from said first MR image recorded by a scanner, wherein the group of image points includes at least one interesting image point which corresponds to one of the unknown property values, wherein each unknown property value represents an attenuation value;
providing a plurality of training pairs, wherein a structure of the training pairs corresponds to the structure of said reference pairs, and wherein first and second entries of the respective training pairs are known; and
determining an assignment between the first entries and the second entries of the training pairs by machine learning, and predicting an attenuation value for an arbitrary image point which corresponds to the at least one interesting image point of the first MR image by applying the determined assignment to one of the second entries of the reference pairs including said arbitrary image point.

* * * * *